United States Patent
Galen et al.

(10) Patent No.: US 7,065,397 B2
(45) Date of Patent: Jun. 20, 2006

(54) MULTI-PARAMETER ACQUISITION OF ECG AND RELATED PHYSIOLOGIC DATA EMPLOYING MULTI-PARAMETER SENSOR AND CONVENTIONAL ECG LEAD CONDUCTORS, AND ENABLED FOR REMOTE OPERATIONAL MANAGEMENT COMMUNICATION

(75) Inventors: Peter M. Galen, McMinnville, OR (US); Martin Baumer, Carlton, OR (US)

(73) Assignee: Inovise Medical, Inc., Portland, OR (US)

( * ) Notice: Subject to any disclaimer, the term of this patent is extended or adjusted under 35 U.S.C. 154(b) by 576 days.

(21) Appl. No.: 10/175,354

(22) Filed: Jun. 18, 2002

(65) Prior Publication Data

US 2003/0105405 A1  Jun. 5, 2003

Related U.S. Application Data

(60) Provisional application No. 60/299,265, filed on Jun. 18, 2001, provisional application No. 60/299,161, filed on Jun. 18, 2001, provisional application No. 60/299,264, filed on Jun. 18, 2001, provisional application No. 60/299,580, filed on Jun. 19, 2001, provisional application No. 60/299,577, filed on Jun. 19, 2001, provisional application No. 60/299,550, filed on Jun. 19, 2001, provisional application No. 60/299,551, filed on Jun. 19, 2001, provisional application No. 60/299,552, filed on Jun. 19, 2001.

(51) Int. Cl.
*A61B 5/02* (2006.01)

(52) U.S. Cl. ........................ 600/513; 439/909

(58) Field of Classification Search ........... 600/372, 600/382–397, 508–509, 513; 439/909
See application file for complete search history.

(56) References Cited

U.S. PATENT DOCUMENTS

| | | |
|---|---|---|
| 4,362,164 A | 12/1982 | Little et al. |
| 4,576,179 A | 3/1986 | Manus et al. |

(Continued)

FOREIGN PATENT DOCUMENTS

WO  WO88/05282  7/1988

(Continued)

OTHER PUBLICATIONS

"Clinically Practical Lead Systems for Improved Electrocardiography: Comparison With Precordial Grids and Conventional Lead Systems" Lux et al., vol. 59, No. 2, pp. 356-363 (Feb. 1979).

(Continued)

*Primary Examiner*—Robert E Pezzuto
*Assistant Examiner*—Kristen Mullen
(74) *Attorney, Agent, or Firm*—Jon M. Dickinson PC; Robert D. Varitz PC

(57) ABSTRACT

ECG-related adaptor/sensor structure and methodology which enables various selectable operational communication to occur both unidirectionally and bidirectionally between the adaptor/sensor structure, and remote structure which is intended to receive ECG-related physiologic data from the adaptor/sensor structure.

4 Claims, 1 Drawing Sheet

U.S. PATENT DOCUMENTS

| | | | |
|---|---|---|---|
| 4,832,608 A * | 5/1989 | Kroll | 439/67 |
| 5,086,776 A | 2/1992 | Fowler, Jr. et al. | |
| 5,307,818 A * | 5/1994 | Segalowitz | 600/509 |
| 5,355,883 A * | 10/1994 | Ascher | 600/394 |
| 5,458,116 A | 10/1995 | Egler | |
| 5,685,317 A | 11/1997 | Sjostrom | |
| 5,687,738 A | 11/1997 | Shapiro et al. | |
| 5,724,984 A * | 3/1998 | Arnold et al. | 600/372 |
| 5,727,549 A | 3/1998 | Suda et al. | |
| 5,813,404 A | 9/1998 | Devlin et al. | |
| 5,819,741 A | 10/1998 | Karlsson et al. | |
| 5,957,866 A | 9/1999 | Shapiro et al. | |
| 6,050,950 A | 4/2000 | Mohler | |
| 6,324,432 B1 * | 11/2001 | Rigaux et al. | 607/62 |
| 6,400,975 B1 * | 6/2002 | McFee | 600/372 |
| 6,454,708 B1 * | 9/2002 | Ferguson et al. | 600/300 |
| 6,572,558 B1 * | 6/2003 | Masakov et al. | 600/483 |

FOREIGN PATENT DOCUMENTS

| | | |
|---|---|---|
| WO | WO94/26164 | 11/1994 |

OTHER PUBLICATIONS

"16-Lead ECG Changes With Coronary Angioplasty", Saetre et al., *Journal of Electrocardiology*, vol. 24 Supplement, pp. 153-162 (1991).

"Optimal ECG Electrode Sites and Criteria for Detection of Asymptomatic Coronary Artery Disease-Update 1990: Multilead ECG . . . ", Selvester et al., pp. 8-18 (Feb. 1992).

"The 12-Lead ECG and the Extent of Myocardium at Risk of Acute Infarction: Anatomic Relationships Among Coronary . . . ", Wagner et al., pp. 16-30.

* cited by examiner

MULTI-PARAMETER ACQUISITION OF ECG AND RELATED PHYSIOLOGIC DATA EMPLOYING MULTI-PARAMETER SENSOR AND CONVENTIONAL ECG LEAD CONDUCTORS, AND ENABLED FOR REMOTE OPERATIONAL MANAGEMENT COMMUNICATION

CROSS-REFERENCE TO RELATED APPLICATIONS

This application claims the priority under 35 U.S.C. § 119 and applicable foreign and international law of the following U.S. Provisional Patent Applications: Ser. No. 60/299,265 filed Jun. 18, 2001, 60/299,161 filed Jun. 18, 2001, 60/299,264 filed Jun. 18, 2001, Ser. No. 60/299,580 filed Jun. 19, 2001, Ser. No. 60/299,577 filed Jun. 19, 2001, Ser. No. 60/299,550 filed Jun. 19, 2001, Ser. No. 60/299,551 filed Jun. 19, 2001, and Ser. No. 60/299,552 filed Jun. 19, 2001, all of which are hereby incorporated by reference in their entireties for all purposes.

BACKGROUND AND SUMMARY OF THE INVENTION

This invention relates to a method and to a system for acquiring multi-parameter physiologic data from a patient. According to the invention, at least two categories of data, one of which is conventional ECG data, are collected contemporaneously from a common anatomy site. Collection, according to a preferred embodiment of the invention, is accomplished using a disposable/discardable unitary sensor component which is designed with appropriate transducers configured to accomplish such multi-parameter data collection. The discardable sensor specifically couples disconnectably to an adaptor which is also built in accordance with the invention, which adaptor makes direct communication connection with selected conductors at the distal ends of conventional ECG lead conductors.

The proposed sensor, in this preferred form, is patient specific, and as mentioned above, is discardable and appropriately organized internally with a chosen set of data-collection transducer structures so that it can be employed essentially at a single, localized anatomical site for accomplishing the desired multi-parameter data collection. According to the invention, one of the data parameters always collected includes ECG data. Other parameters, of which there may be more than one, might include, for example, sound/phono data, orientation/position (of subject in space) data, and other. In this setting, there are several kinds of situations now to be discussed generally below which lead to a desire to be able, for operational management purposes, to communicate either unidirectionally or bidirectionally between remote equipment and the sensor unit, or part, of the present invention. For example, such communication might take place between such a sensor and a remote unit which is charged with the activity of gathering ECG and other data for the purpose of interpreting aspects of a subject's heart behavior, and/or simply for gathering and presenting that data in visual or other reviewable form. Most especially, communication of the kinds just generally mentioned can be employed to tune and adjust appropriately provided tunable structure in a sensor so that performance is as precise and accurate and predictable as possible, and/or to inquire about operational capability and statuses of various components that may be present in a data-collection sensor.

Speaking a bit more specifically, it is often desirable to have the capability, at the time that a data-collection procedure is to be performed, to "tune" specific characteristics within the circuitry of one or both units proposed according to the present invention (adaptor and sensor) so as to prepare for optimal performance. Accordingly, in one embodiment of the present invention there is featured an organization which permits precisely this kind of a tuning operation. An implementation of the invention in this setting is described herein, for illustration purposes, in conjunction with tuning the operation of a filter/gain circuit that is employed with a sound/phono microphone transducer charged with the responsibility of gathering sound data from a subject. This illustration which is specifically chosen for discussion herein is but an indication of the capabilities of this feature of the present invention to allow for sophisticated pre-performance adjustments.

An interesting feature and offering with regard to this capability of the invention is a structural and operational organization according to the invention which allows for tuning control signaling to be accomplished through the transmission of control signals over existing, conventional ECG lead conductors which extend to the adaptor/sensor assembly of the invention. There is no requirement for the presence of any additional external wiring. Control signals, that is, for example, tuning-control signals, can be transmitted over the same line designed to carry data parameter signals in a manner which causes no cross-talk interference between these two categories of signals.

Considering the offerings and advantages presented by another embodiment of the invention, there may be circumstances and reasons in particular applications where it may be important to initiate a remote interrogation of certain operational parameters of circuitry within the adaptor/sensor of this invention. For example, it may be useful in certain situations to send an interrogation signal to a connected adaptor/sensor pair to determine that they are, in fact, compatibly coupled units. Certain doubts which might exist about whether, for example, an attached sensor or component within it is/are prepared to operate correctly, including correct operation of an installed battery power source, can be cleared through intelligent interrogation before data collection begins.

Just as was mentioned immediately above, in this embodiment also of the present invention, interrogation communication can take place within the practice of the present invention entirely over conventional ECG lead conductors, without the necessity for providing or installing additional signal wiring. One will note that, with respect to this modification which deals with interrogation, bidirectional communication is enabled whereby the request for information can be sent to the adaptor/sensor pair of this invention from a remote location, with one or more appropriate responses returned from the adaptor/sensor pair to that same or another remote location.

While the mentioned preferred form of the invention includes a disconnectable, and even patient-specific discardable, sensor, it is entirely possible to implement and practice the invention in a setting where disconnectability and discardability are not present, and where the structures of a sensor and an adaptor, as described and illustrated herein, are integrated into a single, nondiscardable unit. Such a modified form of the invention is mentioned more specifically below in conjunction with what is shown in FIG. 1. This unified structure is also referred to herein as an adaptor/sensor structure.

These and other features and advantages which are attained by the present invention will become more fully apparent as the description which now follows is read in conjunction with the accompanying drawings.

DETAILED DESCRIPTION, AND BEST MODE FOR CARRYING OUT, THE INVENTION

Figure 1:
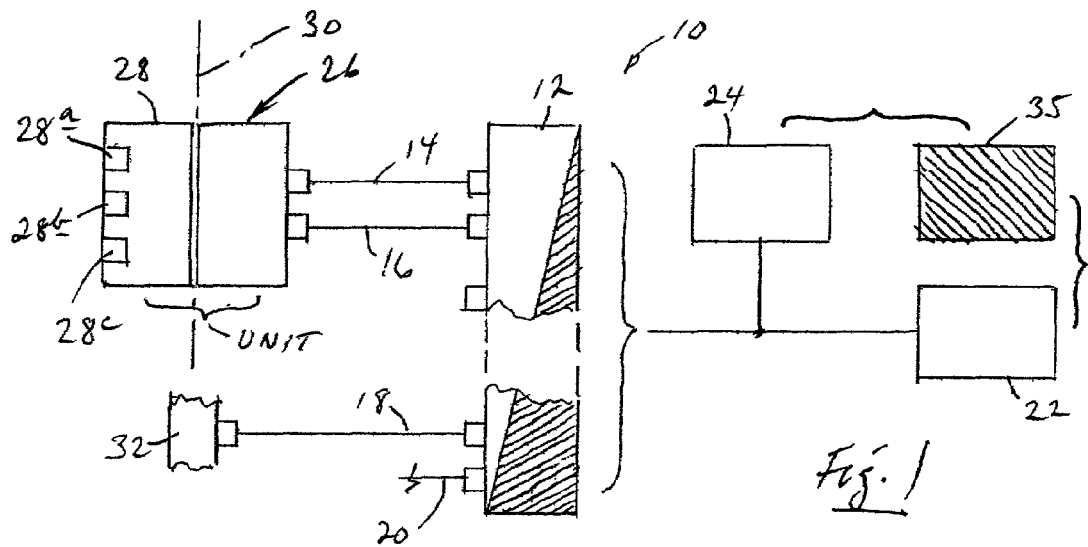
FIG. 1 is a block/schematic diagram illustrating an ECG-data-related system for gathering both ECG and other-parameter data from a subject utilizing an adaptor/sensor pair constructed in accordance with the present invention. This pair allows for remote communication, including bidirectional communication, with a remote communicator which is pictured in FIG. 1 in a shaded rectangle operationally gathered with other remote structure by a pair of brackets. A bracket marked "UNIT" in FIG. 1 illustrates a modified form of the invention wherein the adaptor/sensor structures are unified.

Turning attention now to the drawings, and referring first of all to FIG. 1, here illustrated generally at 10 is a system employing the present invention to gather, in addition to conventional ECG data, one or more other categories of data, such as sound data and spatial-orientation data, helpful in examining the condition and functioning of subject's heart. Centered in FIG. 1 as a fragmented block 12 are conventional ECG lead conductors, with this block being shaded diagonally to highlight the fact that various different conventional styles of ECG conductors can be employed. The shaded area, for example, represents one style of lead conductors, and the unshaded portion of block 12 represents another style. On the left side of this block in FIG. 1 are shown some small rectangles which represent points of connection for outwardly extending conductor leads, four of which are shown at 14, 16, 18 and 20 in FIG. 1.

Illustrated to the right of FIG. 1 as being connected appropriately to what can be thought of as the output side of block 12 are a conventional cardiograph machine 22, and, just for illustration purposes, a data interpretation unit 24. The exact constructions of these two structures (22, 24) form no part of the present invention, and thus are neither illustrated nor discussed in any detail herein.

As shown in FIG. 1, conductor leads 14, 16 extend from block 12 to a block 26 which is referred to herein both as an adaptor, and as a first part. Disconnectably connected (preferably) to adaptor 26 is a sensor shown in block form at 28. Disconnectable connectivity thus allows sensor 28 to be employable as a patient-specific unit. Adaptor 26 and sensor 28 are coupled through appropriate physical interface conductor structure (not specifically shown in FIG. 1) with connection between these two units effectively residing in a region of joinder which is represented by dash-dot line 30 in FIG. 1.

As was mentioned earlier, the bracket marked "UNIT" in FIG. 1 represents a modified form of the invention wherein the adaptor and sensor componentry is integrated into a single unit.

Included within sensor 28 in the illustration now being given are three transducers 28a, 28b, 28c which are employed to gather different kinds of data in accordance with practice of the invention. Transducer 28a is designed to collect sound data, transducer 28b conventional ECG data, and transducer 28c spatial-orientation data. Such data, in accordance with the present invention, in its entirety, is communicated outwardly from the connected adaptor and sensor utilizing only conventional ECG lead conductors, such conductors 14, 16 mentioned above.

Lead conductor 18 is shown connected to a fragmentary illustration at 32 which is intended to represent the right leg of a subject. This connection is most frequently employed in the gathering of ECG data to act as a reference point electrically with regard to the collection of ECG data. It should be noted, and it is known, that the so-called right-leg reference as a reference connection could be replaced with another type of connection. The specific site for such a reference connection herein is not part of the present invention.

The other leads, only one of which is shown, at 20, that form part of lead conductors 12 extend appropriately for connection to other points on the anatomy of a subject where data is being collected.

Also included in the system of FIG. 1 is what is referred to herein as a remote communicator 35. This communicator is represented as a shaded rectangle in FIG. 1, and is gathered operationally with the structures represented by blocks 22, 24 by a pair of brackets. Communication sent from and/or received by structure 35 may relate to activity that is associated with one or both of the structures pictured as blocks 22, 24. Fundamentally, and as now will be described with respect to two specific embodiments, various kinds of useful communication are enabled between block 35 and componentry within one or both of adaptor 26 and/or sensor 28.

Figure 2:
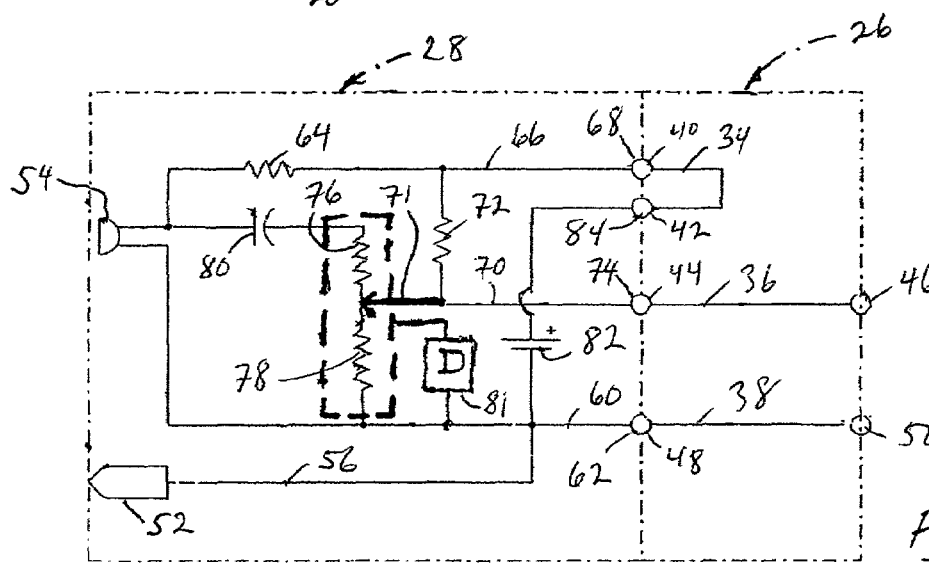
FIG. 2 is a drawing which illustrates internal circuitry present, according to one embodiment of the invention, in the adaptor and sensor paired units constructed according to the present invention. These units are shown, as they were in FIG. 1, in an interconnected condition.

One of the two specific embodiments now to be described is pictured in FIG. 2, and so attention is now directed to that figure. Here one can see one form of internal structural circuitry that exists in adaptor 26 and sensor 28, and how the circuitry present in these two parts comes together as a cooperative co-action circuit when the two units (adaptor/sensor) are disconnectably connected, as is pictured in all of the drawing figures.

Focusing attention now on FIG. 2 along with FIG. 1, adaptor 26 contains internal conductor circuitry including conductors 34, 36, 38. Conductor 34 bridges between two terminals shown at 40, 42 in FIG. 2. Conductor 36 extends between two terminals 44, 46 that are provided in adaptor 26. Conductor 38 extends between and connects two terminals 48, 50 also provided in adaptor 26. Previously mentioned conductor 14 is adapted for connection directly to terminal 46, and conductor 16 to terminal 50.

Included within sensor 28 are an ECG electrode, or transducer, 52, and an appropriate microphone, or transducer, 54. These two transducers are located on and with respect to the body of sensor 28 in such a manner that they can appropriately "engage" a selected local site on the surface of a person's body.

Electrode 52 is connected through a conductor 56, and through a conductor 60, to a terminal 62 in the sensor. Terminal 62 connects with terminal 48 (as shown) when the adaptor and sensor are interconnected as pictured in FIG. 2.

The two output sides of microphone 54 are connected as shown, with the lower side being directly connected to conductor 60, and the upper side being connected through a resistor 64 and a conductor 66 to a terminal 68 which is provided in the sensor. Terminal 68 connects directly with previously-mentioned terminal 40 in adaptor 26 when the adaptor and sensor are interconnected as shown in FIG. 2.

Extending between conductor 66 and a conductor 70 is a resistor 72. The right end of conductor 70 in FIG. 2 connects to a terminal 74 provided in sensor 28, and the left end of conductor 70 connects to a controllable element 71 which connects, in turn, to, and defines, the operative junction that exists between two more resistors (relatively variable) shown at 76, 78. The arrangement shown including element 71 and resistors 76, 78 function as a controllable voltage divider. Control can be implemented herein by remote signaling according to the invention as will shortly be explained. Terminal 74 connects directly with previously mentioned terminal 44 in adaptor 26 under circumstances, such as is pictured in FIG. 2, with the sensor and adaptor interconnected. The lower end of resistor 78 connects with previously-mentioned conductor 60, and the upper end of resistor 76 connects through a filter capacitor 80 to the upper side of microphone 54 in FIG. 2.

Completing a description of what is shown in FIG. 2, at 81 in FIG. 2, labeled D, is an appropriate response structure (decoding element) capable of responding to a remotely transmitted control signal from block 35 (FIG. 1), effectively over conductor 60 to perform an adjustment of the arrangement including elements 71, 76, 78. Such an adjustment operates to change the operating characteristic of the filter/gain circuit which includes these three elements along with capacitor 80. There are many different structures and ways in which the "tuning"/adjustment arrangement now being described can actually be built, and all of these ways are well within the skill level of those skilled in the relevant art. Accordingly, no details of this specific tuning arrangement are included herein.

It suffices to say that an appropriate control signal, generated and transmitted from a remote site can cause a response in decoding element 81, and in particular a response which creates an adjustment in the character of the voltage divider made up of elements 71, 76, 78. Such an adjustment is effective to change the operating parameters of microphone 54. Importantly and interestingly, the remote control "tuning" capability thus furnished herein can be implemented over one of the already used, conventional ECG lead conductors, without there being any requirement for any additional wiring or cabling. Also within the skill level of those skilled in the art is the knowledge of how to encode control signals for transmission in the manner just described for appropriate decoding in element 81, so that control signals are routed and used appropriately for the control just described. The very same encoded signal will produce no interference with any other operation of the circuitry pictured in FIG. 2.

An electrical power source in the form of a battery 82 is furnished within the confines of the body of sensor 28. The positive terminal of this battery is connected to a terminal 84 provided in the sensor, and the negative side of the battery is connected directly to previously mentioned conductor 60. Terminal 84 is directly connected to previously mentioned terminal 42 in adaptor 26 when the adaptor and sensor are connected as shown in FIG. 2.

Finally with respect to FIG. 2, it should be apparent that, while a specific control functionality in the form of permitting tuning and adjustment of the arrangement including elements 71, 76, 78 is disclosed and described herein, it will be understood that other remotely controllable adjustments could be provided for if such were desired. All such remotely controllable adjustments can be implemented in the same manner just described, wherein coded control signals can be transmitted over conventional ECG lead conductors already in use to convey parameter data, without the need for any additional wiring, and without the danger of introducing any conflicting signal behavior within combined the sensor/adaptor assembly.

Figure 3:
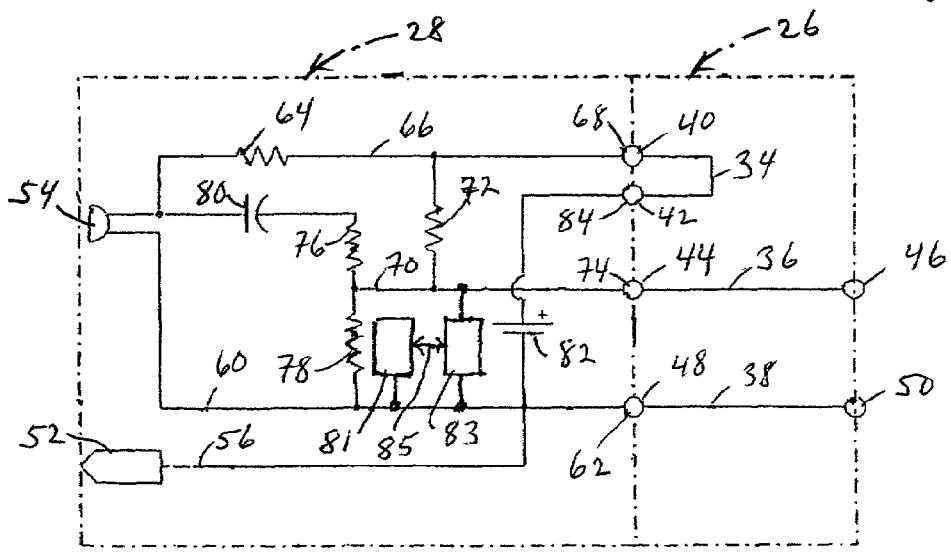
FIG. 3 is very similar to FIG. 2, except that it illustrates here a modified form of cooperative adaptor/sensor pair which enables another category of remote communication between the adaptor/sensor pair and remote communication structure.

Turning attention now to FIG. 3 in the drawings, here there is shown another modified adaptor/sensor pair constructed in accordance with the present invention. In many respects, the internal structures, with respect to a number of components and connections between them, as pictured for these units in FIG. 3, is similar to what is pictured for these same units in FIG. 2, and accordingly, similar reference numerals will be employed and no further detailed discussion given with respect to those components and interconnections which have already been described above.

However, in FIG. 3, there are some notable differences with respect to what is shown in FIG. 2. Directing specific attention now to the region where a difference exists, a description of this difference will include some overlapping description that was given with respect to FIG. 2.

Extending between conductor 66 and conductor 70 is previously described resistor 72. The right end of conductor 70 in FIG. 3 connects to terminal 74 provided in sensor 28, and the left end of conductor 70 connects to the central point of the voltage divider which is made up of two resistors pictured at 76 and 78. Terminal 74 connects directly with previously-mentioned terminal 44 in adaptor 26 under circumstances, such as pictured in FIG. 3, with the sensor and adaptor interconnected.

Shown at 81 in FIG. 3 is an appropriate, conventional, modulator/demodulator structure capable of responding to a remotely transmitted interrogation signal, transmitted effectively over conductor 60 to perform an interrogation regarding the status of battery 82 that is provided in sensor 28. Operatively associated with modulator/demodulator is an appropriate voltage detector 83 which is connected, as shown, across battery 82. Double-headed arrow 85 which extends between the modulator/demodulator and detector 83 represents a communication connection between these two units which permits interrogation of a status of battery 82 and a return of information (a response) through the modulator/demodulator to conductor 60.

An interrogation signal from, for example, previously-mentioned remote block 35, which will be effective to perform the kind of interrogation and response activities just described can be an easily encoded signal, such as a modulated signal, that is readable by the modulator/demodulator, and which can be communicated readily over one of the conventional ECG conductor leads. This communication activity can take place without any cross-talk or other kind of interference occurring between these signals in terms of the operation of the adaptor/sensor assembly.

It should thus now be apparent how the unique features offered by the present invention and set forth earlier herein in general form are in fact provided in very simple and highly reliable structural arrangements that are provided in one or both (if so desired) of the adaptor and sensor units. The same features are also available in a setting where the adaptor and sensor structures and functionalities are unified. Interrogation and response activity can take place with respect to other features that may be incorporated in the adaptor/sensor pair (or unit) according to the invention, and as designers employing this invention address particular areas of other applications.

While the invention has been disclosed in a particular setting, and in particular forms herein, the specific embodiments disclosed, illustrated and described herein are not to be considered in a limiting sense. Numerous variations, some of which have been discussed, are possible. Applicants regard the subject matter of their invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as useful, novel and non-obvious. Other such combinations and subcombinations of features, functions, elements and/or properties may be claimed through amendment of the present claims or through presentation of new claims in this or in a related application. Such amended and/or new claims, whether they are broader, narrower or equal in scope to the originally presented claims, are also regarded as included within the subject matter of applicants' invention.

We claim:

1. Adaptor/sensor apparatus constructed for operative connection to a set of ECG lead conductors having distal ends for collecting, from a subject, plural-parameter physiologic data including EGG data, said apparatus comprising
    an adaptor constructed for direct connection operatively to the distal end of such EGG lead conductors,
    unitary plural-parameter sensor structure organized internally with plural specific parameter sensor devices in the forms of data-collection transducer structures that are designed each to collect, respectively, different physiologic parameter data from a subject's common anatomical site, which sensor structure is discardably connectable operatively to said adaptor to communicate information therewith and therebetween, and
    remotely accessible electrical response structure operatively connected to at least one of said unitary sensor structure and/or said adaptor, capable of being interrogated electrically over conductors in such EGG lead conductors, and to provide, with respect to such an interrogation, an interrogation-response report regarding selected informational characteristics relating to said adaptor and/or sensor structure.

2. Adaptor/sensor apparatus constructed for operative connection to a conventional set of EGG lead conductors having distal ends for collecting, from a subject, plural-parameter physiologic data including EGG data, said apparatus comprising
    an adaptor constructed for direct connection operatively to the distal ends of such EGG lead conductors,
    unitary plural-parameter sensor structure organized internally with plural-specific-parameter sensor devices in the forms of data-collection transducer structures that are designed each to collect, respectively, different physiologic parameter data from a subject's common anatomical site, which sensor structure is discardably connectable operatively to said adaptor to communicate information therewith and therebetween, and
    remotely accessible communication-enabling structure operatively disposed within said unitary sensor structure for the purpose of enabling at least unidirectional operative communication between the sensor structure and an outside communication source for the purpose of addressing selected operational qualities and characteristics of components within the sensor structure.

3. The apparatus of claim 2 wherein said communication-enabling structure permits bidirectional communication.

4. Adaptor/sensor apparatus constructed for operative connection to a set of conventional ECG lead conductors having distal ends for collecting, from a person, plural-parameter physiologic data including ECG data, said apparatus comprising:
    an adaptor which is adapted for direct connection operatively to the distal ends of such ECG lead conductors,
    a unitary plural-parameter sensor organized internally with plural specific parameter sensor devices in the forms of data-collection transducer structures that are designed each to collect, respectively, different physiologic parameter data from a subject's common anatomical site, which sensor is discardably connectable operatively to said adaptor to communicate information therewith and therebetween, and
    remotely controllable tuning structure provided in at least one of said adaptor and unitary sensor, and operable, with the adaptor and sensor discardably interconnected for operation in a cooperative fashion, and in response to a remotely transmitted control signal, to respond to that signal for the purpose of adjusting at least one operational parameter that is controllable within the adaptor or sensor.

* * * * *